United States Patent
Miller et al.

(12)

(10) Patent No.: US 6,174,513 B1
(45) Date of Patent: Jan. 16, 2001

(54) STABILIZATION OF PEPTIDES AND PROTEINS FOR RADIOPHARMACEUTICAL USE

(75) Inventors: Kathleen M. Miller, St. Louis, MO (US); Laurence de La Fourniere, Lyons (FR)

(73) Assignee: MallincKrodt Inc., St. Louis, MO (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/126,545

(22) Filed: Jul. 30, 1998

Related U.S. Application Data

(63) Continuation of application No. 08/893,122, filed on Jul. 15, 1997, now abandoned, which is a continuation of application No. 08/704,036, filed on Aug. 28, 1996, now abandoned, which is a continuation of application No. 08/214,347, filed on Mar. 16, 1994, now abandoned.

(51) Int. Cl.[7] .................. A61K 43/00; A61K 39/395; C07K 16/00
(52) U.S. Cl. .................. 424/1.11; 424/130.1; 424/178.1; 424/179.1; 424/181.1; 424/1.49; 424/1.69; 514/2; 514/975; 530/387.1; 530/389.1; 530/391.3; 436/804

(58) Field of Search ...................... 424/1.11, 9.1, 424/130.1, 178.1, 179.1, 181.1; 514/1, 975; 530/387.1, 389.1, 391.3; 436/804

(56) References Cited

U.S. PATENT DOCUMENTS

| 4,457,916 | * | 7/1984 | Hayashi et al. . |
| 5,328,898 | * | 7/1994 | Greenberg . |
| 5,763,585 | * | 6/1998 | Nag . |
| 5,843,463 | * | 12/1998 | Krivan et al. . |

FOREIGN PATENT DOCUMENTS

WO 91/04057 * 4/1991 (WO) .

OTHER PUBLICATIONS

Wang, Y–C. J. et al. J. Parenteral Sci. Tech. 42 (Suppl): S4–S26, 1988.*

Tiwari, R. P. et al. J. Med. Micro. 22 (2): 115–118, Sep. 1986.*

Hudson and Hay, Practical Immunology, Blackwell Scientific Publications, Great Britain, p. 336, 1980.*

* cited by examiner

*Primary Examiner*—David Saunders
*Assistant Examiner*—Amy DeCloux

(57) ABSTRACT

Surfactants alone or in combination with salts are used to stabilize radiolabeled peptides and proteins contained in diagnostic or therapeutic radiopharmaceutical compositions.

12 Claims, No Drawings

STABILIZATION OF PEPTIDES AND PROTEINS FOR RADIOPHARMACEUTICAL USE

CROSS REFERENCE TO RELATED APPLICATIONS

This application is a continuation of Ser. No. 08/893,122, filed Jul. 15, 1997 (now abandoned), which is a continuation of Ser. No. 08/704,036, filed Aug. 28, 1996 (now abandoned), which is a continuation of Ser. No. 08/214,347, filed Mar. 16, 1994 (now abandoned).

FIELD OF THE INVENTION

This invention relates generally to a novel use of surfactants alone or in combination with salts to stabilize radiolabeled peptides and proteins contained in diagnostic or therapeutic radiopharmaceutical compositions and, more particularly, to the use of one or more surfactants alone or in combination with one or more salts to stabilize radiolabeled peptides, polypeptides or proteins contained in diagnostic or therapeutic radiopharmaceutical compositions for diagnostic tissue imaging or therapeutic use.

BACKGROUND OF THE INVENTION

Scintigraphic imaging and similar radiographic techniques for visualizing tissues in vivo are finding ever-increasing applications in diagnostic procedures. Generally, scintigraphic procedures involve the preparation of radioactive agents which, upon introduction to a biological subject, become localized in the specific organ, tissue, or skeletal structure of choice. When so localized, traces, plots, or scintigraphic images depicting the in vivo distribution of radioactive agents can be generated from data collected by various radiation detectors, such as scintillation cameras. The distribution and corresponding relative intensity of the detected radioactive agent indicate the space occupied by the targeted tissue and may also indicate a presence of receptors, antigens, aberrations, pathological conditions, and the like.

Radioactive agents are also finding increasing applications in therapeutic procedures. As with scintigraphic procedures, the radioactive agents, upon introduction to a biological subject, become localized in the specific organ, tissue, or skeletal structure of choice. Emissions from the radionuclide deliver a therapeutic dose to the targeted tissue.

In general, depending on the type of radionuclide and the target organ or tissue of interest, the compositions of the radioactive agents comprise a radionuclide, a carrier agent designed to target the specific organ or tissue site, possibly various auxiliary agents, e.g. chelating agents, which affix the radionuclide to the carrier, and water or other delivery vehicles suitable for injection into, or aspiration by, the patient, such as physiological buffers, salts, and the like.

Over the years, there has been growing interest in preparing radiolabeled proteins such as macroaggregated albumin ("MAA"), human serum albumin ("HSA"), monoclonal antibodies, or monoclonal antibody fragments for the purpose of diagnosing and treating diseases, such as inflammation, deep vein thrombosis, or cancer.

Recently, the use of radiolabeled peptides for diagnostic and therapeutic applications has attracted much attention. One such radiolabeled peptide is derived from an octapeptide somatostatin analog known as octreotide and is described in U.S. Pat. No. 4,395,403. Octreotide has a very high binding affinity to somatostatin receptors in a variety of human tumors. By linking octreotide to a suitable chelating agent capable of forming a complex with radionuclides, it has been possible to create radiolabeled octreotide which effectively images tumors having somatostatin receptors. Somatostatin analogs containing chelating groups are described in greater detail in UK Patent Publication No. 2,225,579.

Despite the potential usefulness of radiolabeled peptides and proteins, it has been found that such radiolabeled compounds are extremely susceptible to radiolysis, caused by the radionuclide attached thereto for a label.

As used herein, the term radiolysis includes chemical decomposition of the peptide, polypeptide, or protein by the action of radiation emitting from the radionuclide attached for a label. This chemical decomposition can occur in the radiopharmaceutical compositions incubated at room temperature. Often, in the preparation of radiopharmaceutical compositions, these preparations require heating to form the desired product or autoclaving for sterilization. Either of these two processes may accelerate the decomposition of the radiolabeled compounds by the action of radiolysis.

To inhibit or prevent radiolysis, experts have suggested adding a stabilizer such as HSA to the composition (e.g., R. A. J. Kishore, et al., "Autoradiolysis of Iodinated Monoclonal Antibody Preparations," *Int. J. Radiat. Apnl. Instrum.*, Part B, Vol. 13, No. 4, pp. 457–459 (1986) and European Patent Application having International Publication Number WO91/04057), keeping the radiopharmaceutical composition frozen between preparation and administration (e.g., R. L. Wahl, et al., "Inhibition of Autoradiolysis of Radiolabeled Monoclonal Antibodies by Cryopreservation," *J. Nuc. Med.*, Vol. 31, No. 1, pp. 84–89 (1990)), or storing a radiolabeled biological molecule in contact with an ion exchange resin (European Patent Application 0 513 510 A1). These techniques for preventing radiolysis are often not effective or practical when used with many radiolabeled peptides and proteins.

Surfactants have been shown to alter the reactivity of radiolytically generated radicals (e.g. $e^{-1}$ (aq), .OH, .H) towards substrates such as benzene (J. H. Fendler, et al., "Radiation Chemistry of Aqueous Miceller Systems", Report, RRL-3238–364, 12 pp., Avail, Dep. NTIS), pyrimidines (J. H. Fendler, et al., "Radiolysis of Pyrimidines in Aqueous Solutions", *J. Chem. Soc., Faraday Trans.* 1, Vol. 70, No. 7, pp. 1171–9, 1974) and dimethyl viologen cations (M. A. J. Rodgers, D. C. Foyt, and Z. A. Zimek, "The Effect of Surfactant Micelles on the Reaction Between Hydrated Electrons and Dimethyl Viologen", *Radiat. Res.*, Vol. 75, No. 2, p. 296–304, 1978). Cationic, nonionic, and anionic surfactants have been used, at concentrations both below and above the critical micelle concentration. Reaction rates have been observed to decrease, increase, or remain unchanged, depending on the type of surfactant, the substrate used, and the free radical produced by gamma radiolysis.

Surfactants and in particular polyoxyethylene (20) sorbitan monooleate have likewise been said to stabilize dilute protein solutions (e.g., Dr. W. R. Ashford and Dr. S. Landi: "Stabilizing Properties of Tween® 80 in Dilute Protein Solutions" *Bull. Parent. Drug Assoc.*, Vol. 20, pp. 74–81, 1966). Ashford, et al. suggests that such solution stabilization could be applicable to radiolabeled proteins as directed to the prevention of adsorption to glass since adsorption results in a loss of potency of the particular protein solution. Surfactants have also been taught as stabilizers of proteins against denaturing, thus maintaining, for example, their enzymatic activity or their solubility at an air/liquid interface (Y. J. Wang and M. A. Hanson, "Parenteral Formulations of Proteins and Peptides: Stability and Stabilizers", *J. Parent. Sci. Tech.*, Vol. 42, pp. S4–S26, 1988, and references therein). The use of surfactants as stabilizers of large molecules such as radiolabeled protein, polypeptides, or peptides to avoid radiolytic decomposition has not been previously taught.

From the foregoing, it will be appreciated that what is needed in this particular art field are stabilizers for radiolabeled peptides and proteins in a pharmaceutically effective concentration. Thus, it would be a significant advancement in this art field to provide stabilizing agents which substantially inhibit radiolysis of such radiolabeled peptides, polypeptides, and proteins.

Such stabilizers for substantially inhibiting peptide, polypeptide, or protein radiolysis are thereby disclosed and claimed herein.

SUMMARY OF THE INVENTION

The present invention overcomes and prevents the problem of radiolytic decomposition of radiolabeled peptides, polypeptides or proteins that are contained in diagnostic or therapeutic radiopharmaceutical compositions. The present invention discloses the use of surfactants, used alone or in combination with one or more salts, to stabilize radiolabeled peptides, polypeptides or proteins and thereby avoid radiolytic decomposition thereof. These stabilized compounds may be used for the diagnostic imaging of targeted tissues or for therapeutic treatment.

In diagnostic imaging localization, a radiolabeled compound must be easily detectable and highly selective. High selectivity, which is essential in these compounds, means that the diagnostic compound, after having been introduced into the body, accumulates to a greater degree in the target tissue or tissues, e.g. a malignant tumor, than in surrounding tissues. In using peptides, polypeptides or proteins as carrier agents in radiolabeled compounds, the specific high selectivity of the particular carrier agent used provides for the strong accumulation of the diagnostic compound in the target tissue or tissues, such as, for example, in tumors compared with the concentration thereof in non-target tissues.

For therapeutic treatment, the radiolabeled peptide, polypeptide, or protein compound is constructed using high energy beta or alpha emitting isotopes rather than the pure gamma emitters customarily used for diagnostic purposes. These therapeutic agents must have the same high selectivity property as the diagnostic agents to achieve therapeutic treatment of target tissues, such as malignant tumors.

A problem commonly encountered in radiolabeling peptides, polypeptides and proteins overcome by the present invention is that radiolabeled peptides, polypeptides and proteins are highly susceptible to decomposition from radiolysis. This radiolytic decomposition can be accelerated if the radiolabeled preparation is heated or autoclaved.

The present invention overcomes this problem of radiolysis by stabilizing the radiolabeled peptide, polypeptide or protein compound in the diagnostic or therapeutic formulation through the use of one or more suitable surfactants used alone or in combination with one or more suitable salts, to prevent radiolytic decomposition and to preserve the specificity of the compound.

The above-described present invention makes radiolabeled peptides, polypeptides and proteins previously viewed as being difficult to stabilize very attractive for diagnostic purposes as well as for radiotherapy. This method of stabilization of radiolabeled compounds is useful with any radionuclide favorable for imaging or therapy. For diagnostic imaging purposes, the most suitable radionuclides include but are not limited to indium-111, technetium-99 m, iodine-123, gallium-67, and copper-62. Suitable radionuclides for radiotherapy include but are not limited to rhenium-186, rhenium-188, copper-67, iodine-131, copper-67, yttrium-90, dysprosium-165, samarium-153, holmium-166, strontium-89, rhodium-105, and cobalt-60.

Radiolabeling of peptides and proteins can be achieved using various methods known in the art. For example, peptides can be labeled through use of a bifunctional chelate, direct labeling, or covalent binding to a specific functional group of an amino acid side chain. The use of a bifunctional chelate involves covalent attachment of a chelate, which complexes with the radionuclide, to the peptide or protein. Possible bifunctional chelates include diethylene triaminepentaacetic acid (DTPA) and triamine thiolate ($N_3S$) ligands. DTPA may be attached to the peptide or protein by the dicyclic dianhydride method described in U.S. Pat. No. 4,479,930, which is incorporated herein by reference. $N_3S$-type ligands may be attached to the peptide or protein by the methods described in U.S. Pat. No. 4,965,392 incorporated herein by reference.

In direct labeling, the radionuclide binds to the functional group of amino acid side chains present in the peptide or protein. The radionuclide may also bind to reduced forms of a peptide or protein, such as a peptide or protein containing a reduced disulfide bond. One example of direct labeling known in the art is described in U.S. Pat. No. 4,877,868, which is incorporated herein by reference.

Another well known technique for labeling peptides and proteins involves covalently binding the radionuclide to one specific functional group of an amino acid side chain, such as incorporation of iodide into the phenol group of a tyrosine residue.

Commercial products for preparing radiopharmaceuticals are generally provided as lyophilized (freeze-dried) "kits" or as liquid formulations. Lyophilized kits are well known in the art. According to the present invention, lyophilized kits may contain a transfer ligand, such as sodium gluconate or sodium tartrate, a reducing agent, such as tin, depending on the radioisotope that is used, a bulking agent, such as inositol or lactose, the peptide or protein to be labeled, and a surfactant as a stabilizer. Additional stabilizers, such as suitable salts, may be incorporated into the formulation. A solution containing the radioisotope is added to the lyophilized kits prior to patient administration. In some cases, the reconstituted kit may need to be deoxygenated or may be heated or autoclaved.

Liquid formulations usually contain the peptide or protein labeled with the radioisotope in a solution that is ready to be administered to the patient. According to the present invention, the liquid formulation contains a surfactant as a stabilizer. Additional stabilizers, such as suitable salts, may be incorporated into the formulation. The liquid formulation may need to be deoxygenated or may be heated or autoclaved.

The radiolabeled compositions of the invention may be administered parenterally, preferably intravenously, in the form of injectable pharmaceutical solutions or suspensions according to conventional techniques.

Dosages employed in practicing the therapeutic method of the present invention will of course vary depending on the particular condition to be treated, for example the volume of the tumor, the particular chelate employed, the half-life of radioisotope, and the therapy desired. In general, the dose is calculated on the basis of radioactivity distribution to each organ and on observed target uptake.

Due to the unique mechanism of the surfactants employed in the present invention to stabilize the radiolabeled peptide, polypeptide or protein compositions to avoid radiolysis thereof, (which may destroy the ability of the peptides, polypeptides or proteins to bind to specific biological receptors and may alter the biodistribution), the use of radiolabeled compounds for diagnostic imaging or radiotherapy of targeted tissues is now possible with significantly greater ease and success due to greater stability thereof.

It is therefore an object of the present invention to provide a suitable surfactant for stabilizing radiolabeled peptides, -polypeptides and proteins in diagnostic or therapeutic pharmaceutical preparations that are prepared at ambient temperature, or are heated or autoclaved, and are preferably stored at ambient temperature.

DETAILED DESCRIPTION OF THE INVENTION

The preferred surfactant employed in the present invention is polysorbate 80 (polyoxyethylene (20) sorbitan monooleate), also known as "Tween® 80", (registered trademark of Atlas Chemical Industries, Inc.) which is a non-ionic surfactant. Other non-ionic surfactants such as polyethyleneglycol p-isooctylphenylether may be used to stabilize the radiolabeled peptide, polypeptide, or protein compositions. Examples of other types of surfactants that could be used include, but are not limited to, cationic surfactants such as but not limited to cetyltrimethylammonium bromide, anionic surfactants such as but not limited to sodium dodecylsulfate, or zwitterionic surfactants such as but not limited to N-dodecylsultaine.

The advantages of adding one or more surfactants alone or in combination with one or more salts to radiolabeled peptide, polypeptide and protein compounds is to effectively prevent decomposition thereof from radiolysis. Suitable stabilizers combined with suitable salts have likewise been found to increase the stabilization of such radiolabeled compounds. Examples of such suitable salts include but are not limited to NaCl, KCl, $CaCl_2$, and $MgCl_2$. Studies show that the combination of the surfactant polysorbate 80 and NaCl led to improved stabilization of the radiolabeled compounds over that achieved by using polysorbate 80 alone. A summary of the results of this study is illustrated in Table 1 of Example 4 below.

The method of stabilizing radiolabeled compounds of the present invention is described in still greater detail in the illustrative examples which follow.

EXAMPLE 1

Preparation of In-111 Labeled Peptide With No Additives

A stock solution was prepared by dissolving 56 mg trisodium citrate dihydrate, 4 mg citric acid monohydrate, 20 mg gentisic acid, and 100 mg inositol in 10 ml water. The pH was adjusted to 4.0 with 1.0N HCl. The solution was purged for 30 minutes with argon.

A 10 microliter aliquot of a 1 mg DTPA-octreotide [N-(diethylenetriamine-N,N,N',N''-tetraacetic acid-Nu-acetyl)-D-phenylalanyl-L-hemicystyl-L-phenylalanyl-D-tryptophyl-L-lysyl-L-threonyl-L-hemicystyl-L-threoninol cyclic (2–7) disulfide] per 1 ml water solution was transferred into a 5 ml tubing vial and then 1 ml of the stock solution and 20 microliter of a In-111/0.05M HCl solution were added, yielding a solution containing 4.2 mCi/ml. A 0.5 ml aliquot of this preparation was transferred to another 5 ml tubing vial and stored at room temperature. The remaining 0.5 ml of the reaction solution was autoclaved for 15 minutes at 121° C.

The radiochemical yield of the In-111 DTPA-octreotide was determined using reverse phase HPLC with a mobile phase gradient. The column used was an Absorbosphere $C_{18}$ column, 5 micrometer, 260 mm×4.6 mm. Mobile phase A contained 40:60 methanol:water, 50 mM sodium acetate, pH 5.5. Mobile phase B contained 80:20 methanol:water, 50 mM sodium acetate, pH 5.5. The gradient was a linear gradient from 100% A to 100% B over 20 minutes. The retention time of the In-111 DTPA-octreotide was between 19.4–19.8 minutes. Peptide decomposition products eluted prior to the In-111 DTPA-octreotide peak or eluted after the peak when the mobile phase reached 100% B.

The radiochemical purity of the room temperature preparation and the autoclaved preparation were measured by HPLC initially after preparation, after 3 days, and after 4 days. The RT preparation had 98%, 90%, and 86% radiochemical purity values and the autoclaved preparation had 93%, 89%, and 90% radiochemical purity values as illustrated in Table 1 of Example 4 below.

EXAMPLE 2

Preparation of In-111 Labeled Peptide With Polysorbate 80

The procedure for this preparation was the same as for the preparation in Example 1 except that 20 microliters of 20% Polysorbate 80 in ethanol was added to the 1 ml solution of In-111 DTPA-octreotide. The vial contained 4.97 mCi/ml. The preparation was divided in half, with 0.5 ml kept at room temperature and 0.5 ml autoclaved for 15 minutes at 121° C. The radiochemical purity of the In-111 DTPA-octreotide was measured using the HPLC method described in Example 1.

The radiochemical purity for these samples initially after preparation, after 3 days, and after 4 days were measured by HPLC. The RT preparation+Polysorbate 80 had radiochemical purity values of 97%, 97%, and 97% and the autoclaved preparation+Polysorbate 80 had radiochemical purity values of 94%, 94%, and 92% as illustrated in Table 1 in Example 4 below.

EXAMPLE 3

Preparation of In-111 Labeled Peptide With NaCl

The procedure for this preparation was the same as for the preparation in Example 1 except that 7 mg NaCl was added to the 1 ml solution of In-111 DTPA-octreotide. The vial contained 4.92 mCi/ml. The preparation was divided in half, with 0.5 ml kept at room temperature and 0.5 ml autoclaved for 15 minutes at 121° C. The radiochemical purity of the In-111 DTPA-octreotide was measured using the HPLC method described in Example 1.

The radiochemical purity for these samples after initial preparation, after 3 days, and after 4 days were 97%, 97%, and 97% for the RT preparation+NaCl and were 94%, 93%, and 91% for the autoclaved preparation+NaCl.

EXAMPLE 4

Preparation of In-111 Labeled Peptide With Polysorbate 80 and NaCl

The procedure for this preparation was the same as for the preparation in Example 1 except that 20 microliters of 20%

Polysorbate 80 in ethanol and 7.0 mg of NaCl was added to the 1 ml solution of In-111 DTPA-octreotide. The vial contained 4.83 mCi/ml. The preparation was divided in half, with 0.5 ml kept at room temperature and 0.5 ml autoclaved for 15 minutes at 121° C. The radiochemical purity of the In-111 DTPA-octreotide was measured using the HPLC method described in Example 1.

The radiochemical purity for these samples initially after preparation, after 3 days, and after 4 days were 98%, 97%, and 97% for the RT preparation+Polysorbate 80+NaCl and were 95%, 94%, and 93% for the autoclaved preparation+ Polysorbate 80+NaCl.

TABLE 1

RADIOCHEMICAL PURITY VALUES FOR PREPARATIONS FROM EXAMPLES 1 THROUGH 4.

|  | Initial | t = 3d | t = 4d |
|---|---|---|---|
| A. Radiochemical Purity of Room Temperature Preparations: | | | |
| RT | 98% | 90% | 86% |
| RT + Polysorbate 80 | 97% | 97% | 97% |
| RT + NaCl | 97% | 97% | 97% |
| RT + Polysorbate 80 + NaCl | 98% | 97% | 97% |
| B. Radiochemical Purity of Autoclaved Preparations: | | | |
| Autoclaved | 93% | 89% | 90% |
| Autoclaved + Polysorbate 80 | 94% | 94% | 92% |
| Autoclaved + NaCl | 94% | 93% | 91% |
| Autoclaved + Polysorbate 80 + NaCl | 95% | 94% | 93% |

EXAMPLE 5

Preparation of In-111 Labeled Peptide Without And With Polysorbate 80

A stock solution was prepared by dissolving 1.5 mg gentisic acid and 33.5 mg sodium gentisate in 10 ml water. The pH of the solution was 4.2. The solution was purged for 30 minutes with argon.

A 10 microliter aliquot of a 1 mg DTPA-octreotide [N-(diethylenetriamine-N,N,N',N"-tetraacetic acid-N"-acetyl)-D-phenylalanyl-L-hemicystyl-L-phenylalanyl-D-tryptophyl-L-lysyl-L-threonyl-L-hemicystyl-L-threoninol cyclic (2–7) disulfide] per 1 ml water solution was transferred into a 5 ml tubing vial and then 1 ml of the stock solution and 20 microliters of an In-111/0.05M HCl solution were added, yielding a solution containing 5.65 mCi/ml. A 0.5 ml aliquot of this preparation was transferred to a 5 ml tubing vial and stored at room temperature. The remaining 0.5 ml was autoclaved for 15 minutes at 121° C.

The radiochemical purity of this preparation was determined by HPLC as described in Example 1.

A second preparation was made as described above except that 20 microliters of a 20% Polysorbate 80 solution in ethanol was added to the 1 ml reaction solution. To this solution was added 100 microliters of In-111/0.05M HCl, yielding a solution containing 5.9 mCi/ml. The solution was divided in half, and 0.5 ml of the solution in a 5 ml tubing vial was autoclaved for 15 minutes at 121° C.

The radiochemical purity for the autoclaved samples after initial preparation, after 1 day, and after 4 days is tabulated below.

| Time | Initial | t = 3d | t = 4d |
|---|---|---|---|
| Autoclaved Preparation | 91% | 88% | 79% |
| Autoclaved Preparation + Polysorbate 80 | 96% | 95% | 95% |

After the radiolabeled peptide, polypeptide, or protein is stabilized according to the procedure described above, the compound is used with a pharmaceutically acceptable carrier in a method of performing a diagnostic imaging procedure using a scintillation camera or like device or a therapeutic treatment. This procedure involves injecting or administering, for example in the form of an injectable liquid, to a warm-blooded animal an effective amount of the present invention and then exposing the warm-blooded animal to an imaging procedure using a suitable detector, e.g. a scintillation camera. Images are obtained by recording emitted radiation of tissue or the pathological process in which the radioactive peptide, polypeptide, or protein has been incorporated, thereby imaging at least a portion of the body of the warm-blooded animal. Pharmaceutically acceptable carriers for either diagnostic or therapeutic use include those that are suitable for injection or administration such as aqueous buffer solutions, e.g. tris (hydroxymethyl) aminomethane (and its salts), phosphate, citrate, bicarbonate, etc., sterile water for injection, physiological saline, and balanced ionic solutions containing chloride and/or bicarbonate salts of normal blood plasma cations such as $Ca^{2+}$, $Na^+$, $K^+$ and $Mg^{2+}$. Other buffer solutions are described in *Remington's Practice of Pharmacy*, 11th edition, for example on page 170. The carriers may contain a chelating agent, e.g. a small amount of ethylenediaminetetraacetic acid, calcium disodium salt, or other pharmaceutically acceptable chelating agents.

The concentration of radiolabeled peptide, polypeptide, or protein and the pharmaceutically acceptable carrier, for example in an aqueous medium, varies with the particular field of use. A sufficient amount is present in the pharmaceutically acceptable carrier in the present invention when satisfactory visualization of the targeted tissue is achievable or therapeutic results are achievable.

The stabilized compositions of the present invention are administered to the warm-blooded animals so that the composition remains in the living animal for about six to seven hours, although shorter and longer residence periods are normally acceptable.

After consideration of the above specification, it will be appreciated that many improvements and modifications in the details may be made without departing from the spirit and scope of the invention. It is to be understood, therefore, that the invention is in no way limited, except as defined by the appended claims.

What is claimed is:

1. A diagnostic composition suitable for administration to a warm-blooded animal comprising a diagnostically effective amount of a radiolabeled peptide, radiolabeled polypeptide or radiolabeled protein, the peptide, polypeptide or protein having biological receptor binding activity and labeled with a diagnostically effective radionuclide; and one or more surfactants in an amount sufficient to prevent radiolysis during storage of said radiolabeled peptide, radiolabeled polypeptide, or radiolabeled protein, the composition being capable of administration to an animal to produce diagnostic imaging thereof.

2. The diagnostic composition of claim 1 wherein said one or more surfactants are selected from the group consisting of cationic, anionic, nonionic and zwitterionic surfactants.

3. The diagnostic composition of claim 1 wherein the composition additionally comprises one or more salts.

4. The diagnostic composition of claim 2 wherein the composition additionally comprises one or more salts.

5. The diagnostic composition of claim 3, wherein said one or more salts are selected from the group consisting of NaCl, KCl, CaCl$_2$, and MgCl$_2$.

6. The diagnostic composition of claim 3, wherein said one or more surfactants is polysorbate 80 and said one or more salts is NaCl.

7. A therapeutic composition suitable for administration to a warm-blooded animal comprising a therapeutically effective amount of a radiolabeled peptide, radiolabeled polypeptide or radiolabeled protein, the peptide, polypeptide or protein having biological receptor binding activity and labeled with a therapeutically effective radionuclide; and one or more surfactants in an amount sufficient to prevent radiolysis during storage of said therapeutic composition, the composition being capable of administration to an animal to produce therapeutic effects on targeted tissues.

8. The therapeutic composition of claim 7, wherein said one or more surfactants are selected from the group consisting of cationic, anionic, nonionic and zwitterionic surfactants.

9. The therapeutic composition of claim 7, wherein the composition additionally comprises one or more salts.

10. The therapeutic composition of claim 8, wherein the composition additionally comprises one or more salts.

11. The therapeutic composition of claim 9, wherein said one or more salts are selected from the group consisting of NaCl, KCl, CaCl$_2$ and MgCl$_2$.

12. The therapeutic composition of claim 9, wherein said one or more surfactants is polysorbate 80 and said one or more salts is NaCl.

* * * * *